United States Patent [19]
Kirby

[11] 3,993,698
[45] Nov. 23, 1976

[54] HERBICIDAL 2-ALKYL GLYCEROL DERIVATIVES
[75] Inventor: Peter Kirby, Bearsted, England
[73] Assignee: Shell Oil Company, Houston, Tex.
[22] Filed: Feb. 10, 1975
[21] Appl. No.: 548,724

[30] Foreign Application Priority Data
Feb. 21, 1974 United Kingdom............... 7902/74

[52] U.S. Cl.............................. 260/611 A; 71/124; 424/339
[51] Int. Cl.² ........................................ C07C 43/20
[58] Field of Search................................ 260/611 A

[56] References Cited
UNITED STATES PATENTS
2,973,388   2/1961   Riemschneider ........... 260/611 A X FOREIGN PATENTS OR APPLICATIONS
1,599,577   8/1970   France ............................ 260/611 A
1,293,546   10/1972  United Kingdom
1,023,784   3/1966   United Kingdom............. 260/611 A Primary Examiner—Bernard Helfin

[57] ABSTRACT

Certain derivatives of 2-alkyl glycerols are useful as herbicides.

5 Claims, No Drawings

HERBICIDAL 2-ALKYL GLYCEROL DERIVATIVES

SUMMARY OF THE INVENTION

This invention relates to 2-alkyl glycerol derivatives which are biologically active, in particular possessing herbicidal, plant growth regulant and fungicidal properties.

DESCRIPTION OF THE PREFERRED EMBODIMENT

Accordingly the present invention provides 2-alkyl glycerol derivatives having the general formula:

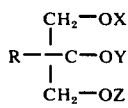

wherein R represents an alkyl group; and X represents optionally substituted benzyl, Y represents hydrogen, alkyl, alkenyl or optionally substituted benzyl and Z represents alkyl, alkenyl or optionally substituted benzyl.

Because of their herbicidal activity level, preferred 2-alkyl glycerol derivatives of this invention are those wherein R contains from 1 to 6 carbon atoms, the alkyl and alkenyl groups represented by Y and Z each contain up to six carbon atoms and the aralkyl groups represented by X, Y and Z are optionally substituted by one or more of chlorine, bromine, fluorine or alkyl of 1 to 4 carbon atoms.

By reason of their high level of herbicidal activity a particularly preferred subclass is that wherein R is alkyl of 1 to 6 carbon atoms, X is benzyl or benzyl substituted by from 1 to 2 of chlorine, fluorine or methyl, Y is alkyl of 1 to 6 carbon atoms or is allyl, and Z is alkyl of 1 to 6 carbon atoms or is benzyl or a substituted benzyl defined by X. Particular species of this subclass that are of interest are:

1,2-dimethoxy-2-methyl-3-benzyloxypropane
1,2-dimethoxy-2-methyl-3-(methylbenzyloxy) propane
1,2-dimethoxy-2-ethyl-3-benzyloxypropane It will be appreciated that many of the 2-alkyl glycerol derivatives of the invention may exhibit optical isomerism. The individual isomers of these compounds together with isomeric mixtures thereof are included within the scope of the present invention.

The invention includes also a process for the preparation of those 2-alkyl glycerol derivatives of formula I which comprises reacting a mono- or di-hydroxy compound of formula:

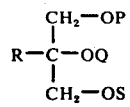

wherein R is an alkyl group, and one or two of the groups P, Q and S is an aralkyl group and the remaining one or two groups is/are hydrogen atoms with a compound of formula:

$$Y^1\text{-Halogen} \quad (III)$$

or $$Y^1\text{-NCO} \quad (IV)$$

wherein $Y^1$ is an optionally substituted alkyl, alkenyl, or aralkyl group. The hydroxy compound (II) is preferably used in the form of an alkali metal salt, suitably the sodium salt. When reactant (III) is used an organic solvent such as dimethyl formamide is conveniently employed and when reactant (IV) is required the reaction is preferably carried out in the presence of an organic base for example a tertary amine such as triethylamine.

The mono-aralkyl dihydroxy derivative which is not included within the scope of the present invention but which may be used as a starting material for many of the compounds according to the invention can be prepared according to the method disclosed by Howe and Malkin Journal of Chemistry Society 1951, 2666.

As mentioned above the 2-alkyl glycerol derivatives of the invention exhibit herbicidal and plant growth regulant properties and the invention therefore includes biologically active compositions comprising a carrier or a surface active agent, or both a carrier and a surface-active agent, and as active ingredient at least one 2-alkyl glycerol derivative of the invention.

The term 'carrier' as used herein means a material, which may be inorganic or organic and of synthetic or natural origin, with which the active compound is mixed or formulated to facilitate its application to the plant seed, soil or other object to be treated, or its storage, transport or handling. The carrier may be a solid or a fluid. Any of the material usually applied in formulating pesticides may be used as carrier.

Suitable solid carriers are natural and synthetic clays and silicates for example natural silicas such as diatomacious earths; magnesium silicates, for example, talcs; magnesium aluminium silicates, for example, attapulgites and vermiculites, aluminium silicates, for example, kaolinites, montmorillinites and micas; calcium carbonates; calcium sulphate; synthetic hydrated silicon oxides and synthetic calcium or aluminium silicates; elements such as for example, carbon and sulphur; natural and synthetic resins such as for example, coumarone resins, polyvinyl chloride and styrene polymers and copolymers; solid polychlorophenols; bitumen; waxes such as for example, beeswax, paraffin wax, and chlorinated mineral waxes; solid fertilisers, for example superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene toluene and xylene; petroleum fractions such as for example, kerosine, light mineral oils; chlorinated hydrocarbons, such as for example, carbon tetrachloride, perchloroethylene, trichloroethane, including liquefied normally vaporous gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols for example p-octylphenol or p-octylcresol, with ethylene oxide and/or propylene oxide, sulphates or sulphonates of these condensation products; alkali or alkaline earth metal salts, preferably sodium salts, of sulphuric or sulphonic acid esters containing at least 10 carbon atoms in the molecule, for example, sodium lauryl sulphate, sodium secondary alkyl sulphates, sodium salts of sulphonated castor oil, and sodium alkylaryl sulphonates such as sodium dodecylbenzene sulphonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols. Wettable powders are usually compounded to contain 25, 50 or 75% w of toxicant and usually contain, in addition to solid carrier, 3–10% w of a dispersing agent and, where necessary, 0 – 10% w of stabiliser(s) and/or additives such as penetrants or stickers. Dusts are usually formulated as a dust concentrate having a similar composition to that of a wettable powder but without a dispersant, and are diluted in the field with further solid carrier to give a composition usually containing ½ – 10% w of toxicant. Granules are usually prepared to have a size between 10 and 100 BS mesh, and may be manufactured by agglomeration or impregnation techniques. Generally, granules will contain ½ – 25% w toxicant and 0 – 10% w of additives such as stabilisers, slow release modifiers and binding agents. Emulsifiable concentrates usually contain, in addition to the solvent and, when necessary, co-solvent, 10 – 50% w/v toxicant, 2 – 20% w/v emulsifiers and 0 – 20% w/v of appropriate additives such as stabilisers, penetrants and corrosion inhibitors. Suspension concentrates are compounded so as to obtain a stable, non-sedimenting, flowable product and usually contain 10 – 75% w toxicant, 0.5 – 15% w dispersing agents, 0.1 – 10% w or suspending agents such as protective colloids and thixotropic agents, 0 – 10% w of appropriate additives such as defoamers, corrosion inhibitors, stabilisers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

The compositions of the invention may contain other ingredients, for example, protective colloids such as gelatin, glue, casein, gums, cellulose ethers, and polyvinyl alcohol; thixotropic agents e.g. bentonites, sodium poluphosphates; stabilisers such as ethylene diamine tetra-acetic acids, urea, triphenyl phosphate; and stickers, for example non-volatile oils.

Aqueous dispersion and emulsions, for example, compositions obtained by diluting a wettable powder or an emulsifiable concentrate according to the invention with water, also lie within the scope of the present invention. The said emulsions may be of the water-in-oil or of the oil-in-water type, and may have a thick 'mayonnaise'-like consistency.

The 2-alkyl glycerol derivatives of the present invention are of interest as herbicides and particularly as selective herbicides for pre-emergence application to control grass weeds. The invention includes therefore within its scope a method of protecting crops at a locus from competition by grass weeds which comprises applying to the locus a 2-alkyl glycerol derivative or composition of the invention.

The compounds of the invention may be used in admixture with other herbicides and pesticides. In particular they may be mixed with active materials possessing pre-emergence activity against broad-leaf weeds to give herbicide combinations exhibiting broad-spectrum pre-emergence activity. Examples of such active materials are s-triazine derivatives such as 2,4-bis-(isopropylamino)-6-methylthio-s-triazine, or 2-chloro-4-ethylamino-6-isopropylamino-s-triazine, pyridazole derivatives such as 5-amino-4-chloro-2-phenylpyridaz-3-one, or 1,4-naphthaquinone derivatives.

The invention is further illustrated in the following Examples:

EXAMPLE 1

1,3-Dibenzyloxy-2-methylpropan-2-ol a. Preparation of 2-methylglycerol

Methallyl alcohol (20.0g), alumina (20.0g) and tungstic acid (2.0g) in water (100 ml) were heated to 60° C and then hydrogen peroxide (31.6 ml of 30 w/v solution) was slowly added. During the addition the temperature of the mixture was maintained at 60° C by cooling. When the addition was complete the mixture was maintained at 60° C for a further hour and then at 95° C for 2 hours. After cooling the mixture was filtered and the filtrate passed through two columns containing respectively Amberlite IRA 400 and Permutit Zeo-Carb. 225. The solvent was then removed from the solution to give the crude 2-methylglycerol which was not purified further.

b. Preparation of 1,3-dibenzyloxy-2-methylpropan-2-ol

1-Benzyloxymethyl-1-methyl-ethane-1, 2-diol (5g) in dimethylformamide (25 ml) was treated with sodium hydride (0.65g), the reaction mixture was stirred at ambient temperature for 1 h. then at 90° C for 15 min. The reaction mixture was cooled and benzyl chloride (3.3g) added; it was stirred for 4 h. at ambient temperature. The solvent was evaporated and the product isolated by chromatography on silica gel using methylene chloride/ether (9/1) to give the desired product as a colourless oil. The 1,3-configuration was confirmed by n.m.r. which showed the methylene groups of the carbon backbone to be equivalent, hence, establishing the symmetry of the molecule.

Calculated for $C_{18}H_{22}O_3$: C, 76.0; H, 7.1%. Found: C, 76.3; H, 7.8%.

EXAMPLE 2

1,2,3-Tribenzyloxy-2-methylpropane

1 Benzyloxymethyl-1-methylethane-1,2-diol (2g) in dimethyl formamide (25 ml) was treated with a slight excess of sodium hydride (0.6g) at ambient temperature for 1h, then 90° for 15 mins. The product was then treated with benzyl chloride (4g) and 1,2,3-tribenzyloxy-2-methylpropane was isolated by evaporation of the solvent followed by chromatography on silica gel eluted with 9/1 methylene chloride/ether. The desired product was a colourless oil whose structure was confirmed by n.m.r.

Calculated for $C_{25}H_{28}O_3$: C, 78.9; H, 7.5%. Found: C, 80.6; H, 7.6%.

EXAMPLE 3

1-(2,6-Dichlorobenzyloxy)-3-benzyloxy-2-ethylpropan-2-ol 1-(2,6-Dichlorobenzyloxymethyl)-1-methylethane-1,2-diol (14g) in dimethyl formamide (80 ml) was treated with sodium hydride (1.3 g) at ambient temperature and stirred for 12 h. Benzyl chloride (8 g) was then added and the reaction mixture stirred for a further 4 h. The solvent was then evaporated and 1-(2,6-dichlorobenzyloxy)-3-benzyloxy-2-ethylpropan-2-ol isolated as a colourless oil by chromatography on silica gel eluted with 9/1 methylene chloride/ether. The structure was confirmed by n.m.r. techniques.

Calculated for $C_{19}H_{22}O_3Cl_2$: C, 61.8; H, 6.0; Cl, 19.2%. Found: C, 61.7; H, 6.3; Cl, 20.4%.

EXAMPLE 4

1-Methoxy-3-benzyloxy-2-methylpropan-2-ol 1-(Benzyloxymethyl)-1-methylethane-1,2-diol (10 g) and sodium hydride (1.2 g) were stirred together in dimethyl formamide (50 ml) for 12 h; the reaction mixture was then treated with methyl iodide (7.1g) and again stirred for 4 h. The reaction product was then stripped at 100°/1 mm and the residue purified by chromatography on silica gel eluted with 9/1 methylene chloride/ether to give a small forerun of 1,2-dimethoxy-2-methyl-3-benzyloxypropane and then 11 g 1-methoxy-3-benzyloxy-2-methylpropan-2-ol as a colourless oil. The structure was confirmed by n.m.r. techniques.

Calculated for $C_{12}H_{18}O_3$: C, 68.5%; H, 8.6%. Found: C, 68.2%; H, 8.5%.

EXAMPLE 5

1,2-Dimethoxy-2-methyl-3-benzyloxypropane

The method of example 5 was employed but a slight excess of sodium hydride (2.4g) and then methyl iodide (15g) were employed. 1,2-Dimethoxy-2-methyl-3-benzyloxypropane (9.6g) was isolated as the major production in the form of a colourless oil. The structure was confirmed by n.m.r. techniques.

Calculated for $C_{13}H_{20}O_3$: C, 69.6; H, 9.3%. Found: C, 69.3; H, 9.2%.

EXAMPLE 6–26

Following procedures analogous to those used in the previous Examples additional 2-alkyglycerol derivatives were prepared. The physical characteristics and analyses being set out in the following table:

Table 1

| Example No. | Compound | Boiling Point °C/mmHg | Analysis | |
|---|---|---|---|---|
| 6 | 1,3-dibenzyloxy-2-methyl-2-methoxy-propane | 134–5/0.35 | Calculated for $C_{19}H_{24}O_3$ | : C 76.0; H 8.0% |
| | | | Found | : C 75.1; H 8.2% |
| 7 | 1,2-dimethoxy-2-methyl-3-(2-chlorobenzyloxy) propane | 86–7/0.5 | Calculated for $C_{13}H_{19}ClO_3$ | : C 60.4; H 7.4% |
| | | | Found | : C 59.8; H 7.4% |
| 8 | 1,2-dimethoxy-2-methyl-3-(2-methyl-benzyloxy) propane | 75–7/0.25 | Calculated for $C_{14}H_{22}O_3$ | : C 70.5; H 9.3% |
| | | | Found | : C 71.0; H 9.4% |
| 9 | 1-methoxy-2-methyl-3-(2-methylbenzyloxy) propane-2-ol | 90/0.7 | Calculated for $C_{13}H_{20}O_3$ | : C 69.6; H 9.0% |
| | | | Found | : C 69.2; H 9.0% |
| 10 | 1,2-dimethoxy-2-ethyl-3-benzyloxy-propane | 80–82/0.5 | Calculated for $C_{14}H_{22}O_3$ | : C 70.6; H 9.3% |
| | | | Found | : C 70.4; H 9.2% |
| 11 | 1,3-dimethoxy-2-methyl-3-benzyloxy propane | 74/0.4 | Calculated for $C_{13}H_{20}O_3$ | : C 71.2; H 8.5% |
| | | | Found | : C 70.0; H 8.4% |
| 12 | 1,2-diethoxy-2-methyl-3-benzyloxypropane | 98/0.4 | Calculated for $C_{15}H_{24}O_3$ | : C 71.4; H 9.6% |
| | | | Found | : C 71.8; H 9.8% |
| 13 | 1-ethoxy-2-methyl-3-benzyloxypropan-2-ol | 102/0.5 | Calculated for $C_{13}H_{20}O_3$ | : C 69.6; H 9.0% |
| | | | Found | : C 69.5; H 9.1% |
| 14 | 1-allyloxy-2-methyl-3-benzyloxypropan-2-ol | 85/0.6 | Calculated for $C_{14}H_{20}O_3$ | : C 71.2; H 8.5% |
| | | | Found | : C 70.5; H 8.5% |
| 15 | 1,2-dimethoxy-2-ethyl-3-(2,6-dichloro-benzyloxy)propane | 87/0.2 | Calculated for $C_{14}H_{20}O_3Cl_2$ | : C 54.7; H 6.6% |
| | | | Found | : C 57.5; H 6.8% |
| 16 | 2-methyl-2-butoxy-3-benzyloxypropan-2-ol | 109–111/0.4 | Calculated for $C_{15}H_{24}O_3$ | : C 71.4; H 9.6% |
| | | | Found | : C 72.6; H 9.9% |
| 17 | 2-ethyl-1,2-dimethoxy-3-(2-fluorobenzyl-oxy)propane | 83/0.5 | Calculated for $C_{14}H_{21}O_3F$ | : C 65.6; H 8.3% |
| | | | Found | : C 66.5; H 8.4% |
| 18 | 2-ethyl-1,2-dimethoxy-3-(4-fluoro-benzyloxy)propane | 86–88/0.5 | Calculated for $C_{14}H_{21}O_3F$ | : C 65.6; H 8.3% |
| | | | Found | : C 66.5; H 8.4% |
| 19 | 2-ethyl-1-methoxy-3-(2-fluorobenzyloxy)-propan-2-ol | 90–91/0.35 | Calculated for $C_{13}H_{19}O_3F$ | : C 64.4; H 7.9% |
| | | | Found | : C 64.4; H 8.1% |
| 20 | 2-ethyl-1-methoxy-3-(4-fluorobenzyloxy)-propan-2-ol | 87/0.5 | Calculated for $C_{13}H_{19}O_3F$ | : C 64.4; H 7.9% |
| | | | Found | : C 65.5; H 8.2% |
| 21 | 1,2-dimethoxy-2-ethyl-3-(2-chloro-benzyloxy)propane | 86/0.3 | Calculated for $C_{14}H_{21}O_3F$ | : C 61.6; H 7.8% |
| | | | Found | : C 62.0; H 7.7% |
| 22 | 2-ethyl-1-methoxy-3-(2-chlorobenzyloxy)-propan-2-ol | 91–92/0.45 | Calculated for $C_{13}H_{19}O\ Cl$ | : C 60.4; H 7.4; Cl 13.7% |
| | | | Found | : C 60.3; H 7.3; Cl 13.8% |
| 23 | 2-ethyl-1,2-dimethoxy-3-(2-methylbenzyloxy)-propane | 78/0.2 | Calculated for $C_{15}H_{24}O_3$ | : C 71.4; H 9.6% |
| | | | Found | : C 71.6; H 9.7% |

Table 1-continued

| Example No. | Compound | Boiling Point °C/mmHg | Analysis | |
|---|---|---|---|---|
| 24 | 2-ethyl-1-methoxy-3-(2-methylbenzyloxy)-propan-2-ol | 84/0.25 | Calculated for $C_{14}H_{22}O_3$<br>Found | C 70.5; H 9.3%<br>C 71.1; H 9.4% |
| 25 | 2-methyl-1-methoxy-3-benzyloxy-propan-2-ol | 90–91/0.6 | Calculated for $C_{12}H_{17}O_3F$<br>Found | C 63.4; H 7.5%<br>C 62.8; H 7.4% |
| 26 | 1-methoxy-2-propyl-3-(2-fluorobenzyloxy)-propan-2-ol | 84/0.5 | Calculated for $C_{14}H_{21}O_3F$<br>Found | C 65.6; H 8.3%<br>C 65.7; H 8.5% |

EXAMPLE 27

Herbicidal Activity

To evaluate their herbicidal activity, the compounds of the invention were tested using as a representative range of plants: maize, Zea mays (Mz); rice Oryza sativa (R); barnyard grass, Echinochloa crusgalli (BG); pea, Pisum sativum (P); linseed, Linum usitatissium (L); mustard, Sinapis alba (M); and sugar beet, Beta vulgaris (SB).

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of test, viz, soil drench and foliar spray tests. In the soil drench tests the soil in which seedling plants of the above species were growing, was drenched with a liquid formulation containing a compound of the invention, and in the foliar spray tests the seedling plants were sprayed with such a formulation.

The soil used in the tests was a steam-sterilised, modified John Innes Compost mixture in which the peat, by loose bulk, had been replaced by vermiculite.

The formulations used in the tests were prepared by diluting with water and solutions of the compounds in acetone containing 0.4% by weight of an alkylphenol-/ethylene oxide condensate available under the trade name Triton X-155. In the soil spray and foliar spray tests the acetone solutions were diluted with an equal volume of water and the resulting formulations applied at two dosage levels corresponding to 10 and 1 kilograms of active material per hectare respectively in a volume equivalent to 400 liters per hectare. In the soil drench tests one volume of the acetone solution was diluted to 155 volumes with water and the resulting formulation applied at one dosage level equivalent to 10 kilograms of active material per hectare in a volume equivalent to approximately 3,000 liters per hectare.

In the pre-emergence tests untreated sown soil and in the post-emergence tests untreated soil bearing seedling plants were used as controls.

The herbicidal effects of the compounds were assessed visually seven days after spraying the foliage and drenching the soil and eleven days after spraying the soil, and were recorded on a 0–9 scale. A rating 0 indicates no effect on the treated plants, a rating 2 indicates a reduction in fresh weight of stem and leaf of the plants of approximately 25%, a rating 5 indicates a reduction of approximately 55%, a rating 9 indicates a reduction of 95% etc.

The results of the tests are set out below.

Table 2

| Compound under Test (Example No.) | Dosage Kg/ha | Post-Emergence (Plants) | | | | | | | | | | | | | | Pre-Emergence (Seeds) | | | | | | |
|---|---|---|---|---|---|---|---|---|---|---|---|---|---|---|---|---|---|---|---|---|---|---|
| | | Soil Drench | | | | | | | Foliar Spray | | | | | | | Soil Spray | | | | | | |
| | | Mz | R | BG | P | L | M | SB | Mz | R | BG | P | L | M | SB | Mz | R | BG | P | L | M | SB |
| 3 | 5 | 2 | 0 | 6 | 0 | 3 | 0 | 0 | 7 | 1 | 7 | 4 | 6 | 5 | 6 | 0 | 2 | 9 | 1 | 0 | 2 | 2 |
| | 1 | | | | | | | | 1 | 0 | 5 | 1 | 3 | 2 | 3 | 0 | 0 | 9 | 0 | 0 | 0 | 0 |
| 4 | 5 | 5 | 3 | 5 | 6 | 4 | 0 | 2 | 1 | 1 | 3 | 4 | 2 | 4 | 0 | 0 | 0 | 3 | 0 | 0 | 0 | 0 |
| | 1 | | | | | | | | 0 | 0 | 0 | 0 | 1 | 0 | 0 | | | 0 | | | | |
| 5 | 5 | 6 | 7 | 8 | 3 | 6 | 0 | 3 | 1 | 2 | 6 | 1 | 5 | 3 | 3 | 5 | 9 | 9 | 8 | 7 | 5 | 4 |
| | 1 | | | | | | | | | | 3 | | | | | 1 | 6 | 8 | 1 | 2 | 1 | 0 |
| 6 | 5 | 6 | 4 | 7 | 1 | 3 | 0 | 0 | 3 | 3 | 8 | 4 | 6 | 5 | 5 | 5 | 5 | 9 | 0 | 6 | 3 | 0 |
| | 1 | | | | | | | | 0 | 0 | 6 | 0 | 2 | 2 | 0 | 1 | 0 | 4 | 0 | 0 | 0 | 0 |
| 7 | 10 | 6 | 4 | 6 | 2 | 2 | 0 | 0 | 4 | 2 | 7 | 6 | 5 | 8 | 7 | 7 | 9 | 9 | 9 | 7 | 3 | 2 |
| | 1 | | | | | | | | 0 | 0 | 4 | 0 | 0 | 0 | 0 | 1 | 6 | 9 | 7 | 2 | 1 | 0 |
| 8 | 10 | 6 | 5 | 6 | 5 | 3 | 0 | 0 | 6 | 3 | 6 | 6 | 3 | 4 | 4 | 8 | 9 | 9 | 9 | 6 | 6 | 1 |
| | 1 | | | | | | | | 0 | 0 | 5 | 2 | 0 | 0 | 0 | 3 | 7 | 9 | 7 | 5 | 2 | 0 |
| 9 | 10 | 5 | 4 | 6 | 4 | 0 | 0 | 0 | 4 | 2 | 4 | 2 | 6 | 4 | 4 | 7 | 7 | 9 | 8 | 5 | 1 | 1 |
| | 1 | | | | | | | | 0 | 0 | 0 | 0 | 0 | 0 | 0 | 0 | 2 | 7 | 6 | 2 | 0 | 0 |
| 10 | 10 | 7 | 6 | 7 | 4 | 3 | 0 | 1 | 6 | 2 | 7 | 4 | 5 | 4 | 2 | 8 | 9 | 9 | 9 | 7 | 5 | 1 |
| | 1 | | | | | | | | 1 | 0 | 6 | 0 | 0 | 0 | 0 | 0 | 4 | 9 | 7 | 2 | 0 | 0 |
| 12 | 10 | 7 | 6 | 6 | 0 | 0 | 0 | 0 | 4 | 2 | 5 | 4 | 3 | 3 | 0 | 8 | 9 | 9 | 6 | 4 | 1 | 0 |
| | 1 | | | | | | | | | | | | | | | 1 | 3 | 9 | 2 | 1 | 0 | 0 |

We claim as our invention:

1. A 2-alkyl glycerol derivative having the formula

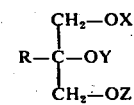

wherein R is methyl or ethyl and X is benzyl, 2-chlorobenzyl, 2-fluorobenzyl, 4-fluorobenzyl, or 2-methylbenzyl and Y and Z each is methyl.

2. A 2-alkyl glycerol derivative according to claim 1 wherein R is methyl; and X is benzyl.

3. A 2-alkyl glycerol derivative according to claim 1 wherein R is methyl; and X is 2-methylbenzyl.

4. A 2-alkyl glycerol derivative according to claim 1 wherein R is ethyl; and X is benzyl.

5. A 2-alkyl glycerol derivative according to claim 1 wherein R is methyl and X is 2-chlorobenzyl.

* * * * *